United States Patent [19]

Meier et al.

[11] Patent Number: 4,868,320

[45] Date of Patent: Sep. 19, 1989

[54] 1,7,9,15-TETRAOXA-4,12-DIAZA-8-SILAS-PIRO-(7.7)-PENTADECANES, A PROCESS FOR THEIR PREPARATON AND THEIR USE

[75] Inventors: Helmut-Martin Meier, Ratingen-Eggerscheidt; Werner Klöker; Armin Sickert, both of Krefeld, all of Fed. Rep. of Germany

[73] Assignee: Bayer Akteingesellschaft, Leverkusen-Bayerwerk, Fed. Rep. of Germany

[21] Appl. No.: 259,596

[22] Filed: Oct. 19, 1988

[30] Foreign Application Priority Data

Oct. 31, 1987 [DE] Fed. Rep. of Germany ....... 3736990

[51] Int. Cl.$^4$ .............................................. C07F 7/10
[52] U.S. Cl. ................................................... 556/408
[58] Field of Search ......................................... 556/408

[56] References Cited

U.S. PATENT DOCUMENTS

| | | | |
|---|---|---|---|
| 2,567,131 | 9/1951 | Speier | 556/408 |
| 3,239,550 | 3/1966 | Murray | 556/408 |
| 3,245,921 | 4/1966 | Friihauf et al. | 556/408 X |
| 3,555,069 | 1/1971 | Frye | 556/408 |

*Primary Examiner*—Paul F. Shaver
*Attorney, Agent, or Firm*—Connolly and Hutz

[57] ABSTRACT

The new 1,7,9,15-tetraoxa-4,12-diaza-8-silaspiro-[7.7]-pentadecanes, which are prepared by reaction of corresponding alkoxysilanes with corresponding alkanolamines, are used above all as hardening accelerators for unsaturated polyester resins and acrylic resins.

2 Claims, No Drawings

1,7,9,15-TETRAOXA-4,12-DIAZA-8-SILASPIRO-(7.7)-PENTADECANES, A PROCESS FOR THEIR PREPARATON AND THEIR USE

This invention relates to new 1,7,9,15-tetraoxa-4,12-diaza-8-silaspiro-[7.7]-pentadecanes, to their production and to their use as accelerators for unsaturated polyester resins.

The new 1,7,9,15-tetraoxa-4,12-diaza-8-silaspiro-[7.7]-pentadecanes according to the invention correspond to formula (I)

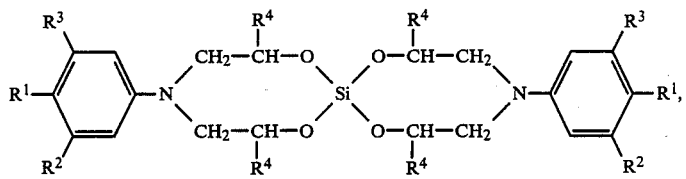

in which
$R^1$, $R^2$ and $R^3$ may be the same or different and represent hydrogen, $C_1$–$C_{18}$ alkyl, $C_5$–$C_8$ cycloalkyl, $C_5$–$C_{14}$ aryl, fluorine, chlorine, bromine or iodine and $R^4$ represents hydrogen, $C_1$–$C_{12}$ alkyl, $C_6$–$C_{12}$ aryl, hydroxy-$C_1$–$C_6$-alkyl, chloro-$C_1$–$C_6$ alkyl, $C_1$–$C_6$-alkoxy-$C_1$–$C_6$-alkyl, $C_6$–$C_{12}$-aryloxy-$C_1$–$C_6$-aryl or $C_2$–$C_6$-acyloxy-$C_1$–$C_6$-alkyl.

Preferred meanings for $R^1$ to $R^3$ are hydrogen, methyl, chlorine, bromine, cyclohexyl, tert.-butyl and phenyl.

Preferred meanings for $R^4$ are hydrogen, methyl, ethyl, hydroxymethyl, chloromethyl, decyl, phenyl, phenyloxymethyl, p-cresyloxymethyl, m-cresyloxymethyl, o-cresyloxymethyl and benzyloxymethyl.

Compounds of formula (I), in which $R^1$ to $R^4$ represent hydrogen and methyl, are particularly preferred.

The present invention also relates to a process for the preparation of the new 1,7,9,15-tetraoxa-4,12-diaza-8-silaspiro-[7.7]-pentadecanes corresponding to formula (I)

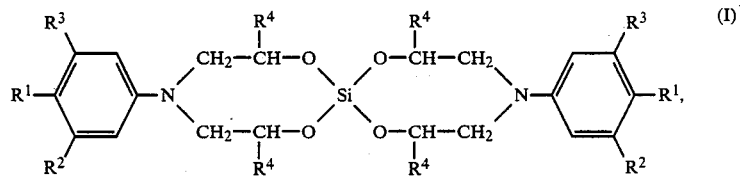

in which
$R^1$, $R^2$ and $R^3$ may be the same or different and represent hydrogen, $C_1$–$C_{18}$ alkyl, $C_5$–$C_8$ cycloalkyl, $C_5$–$C_{14}$ aryl, fluorine, chlorine, bromine or iodine and $R^4$ represents hydrogen, $C_1$–$C_{12}$ alkyl, $C_6$–$C_{12}$ aryl, hydroxy-$C_1$–$C_6$-alkyl, chloro-$C_1$–$C_6$ alkyl, $C_1$–$C_6$-alkoxy-$C_1$–$C_6$-alkyl, $C_6$–$C_{12}$-aryloxy-$C_1$–$C_6$-aryl or $C_2$–$C_6$-acyloxy-$C_1$–$C_6$-alkyl,
characterized in that alkoxysilanes corresponding to formula (II)

$$Si(OR^5)_4 \quad (II)$$

in which $R^5$ is $C_1$–$C_4$ alkyl, are reacted with alkanolamines corresponding to formula (III)

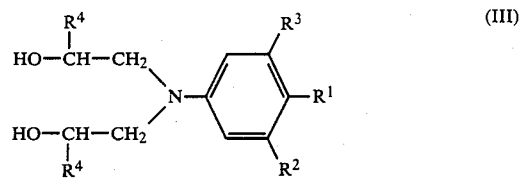

in which $R^1$, $R^2$, $R^3$ and $R^4$ are as defined above, at temperatures of 80° to 160° C. in the presence of alkali and/or alkaline earth alcoholates.

The reaction according to the invention is preferably carried out at temperatures of 100° to 150° C.

The alkanolamines corresponding to formula (III) are normally used in a quantity of 1.5 to 2.5 mol and preferably in a quantity of 1.9 to 2.1 mol per mol alkoxysilane corresponding to formula (II).

The alkali and/or alkaline earth alcoholates used may be the alkanolates or oxyarylates of the alkali or alkaline earth metals, such as sodium, potassium, magnesium and calcium, preferably sodium methylate and/or sodium phenolate. The alcoholates are normally used in quantities of 0.0001 to 0.1% by weight and preferably in quantities of 0.01 to 0.001% by weight.

The process according to the invention may be carried out in accordance with the teaching imparted by EP-OS No. 169 708.

One method of preparing the compounds of formula (I) according to the invention comprises heating the corresponding alkoxysilane of formula (II) with the corresponding alkanolamine of formula (III) under nitrogen to around 100° to 110° C. in the presence of, for example, sodium methylate, keeping the reaction mixture at that temperature for a while (about 2 to 3 hours) and then further heating the reaction mixture to around 140° to 150° C. and again keeping it at that temperature for a while. The alcohol formed is distilled off during the reaction. The desired new compound corresponding to formula (I) remains in the reaction vessel.

The compounds of formula (I) according to the invention may be used as hardening accelerators for unsaturated polyester resins and acrylic resins.

"Unsaturated polyester resins" in the context of the invention are mixtures of 30 to 75 parts by weight of α,β-ethylenically unsaturated polyesters and 70 to 25 parts by weight of unsaturated monomers copolymerizable therewith. They are described, for example, in J. R. Lawrence, "Polyester Resins", Reinhold Publ. Corp.

New York 1960, pages 18 et seq., and in Kunststoff-Handbuch, Vol. VIII ("Polyester"), Carl Hanser Verlag, München 1973, pages 247–312.

The preferred monomer is styrene.

"Acrylic resins" in the context of the invention are polyesters, polyurethanes, polyepoxides, polyols and polyether polyols containing (meth)acryloyloxy groups. These acrylic resins are known (cf. for example DE-OS No. 20 53 683, DE-OS No. 28 38 691 (polyester(meth)acrylates), DE-OS No. 14 47 929, U.S. Pat. No. 3,297,745 (urethane(meth)acrylates), DE-OS No. 19 21 869, U.S. Pat. No. 3,804,735 (epoxy(meth)acrylates), U.S. Pat. No. 3,558,387 (polyol(meth)acrylates) and U.S. Pat. No. 3,380,831 (polyetherpolyol(meth)acrylates).

To reduce viscosity, to increase reactivity or to obtain special properties, the "acrylic resins" mentioned above may also be mixed with copolymerizable, olefinically unsaturated monomers, for example with (meth)acrylates of monohydric alcohols, hydroxyalkyl(meth)acrylates, (meth)acrylamides, styrene, α-methyl styrene, styrenes nucleus-substituted by alkyl groups, divinylbenzene, (meth)acrylonitrile, vinyl chloride, vinylidene chloride, vinyl ethers, vinyl acetate or mixtures thereof. It is of course also possible to polymerize at least one α,β-monoolefinically unsaturated monomer, for example of the type mentioned above, in the presence of the compounds of formula (I) according to the invention.

The new compounds of formula (I) according to the invention may also be used for hardening reactive compositions of the type described in DE-OS No. 36 24 870 and DE-OS No. 36 25 169.

EXAMPLES

Preparation of the compounds according to the invention

EXAMPLE 1

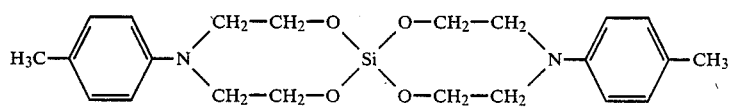

104 g silicic acid tetraethyl ester, 196 g N,N-bis-(β-hydroxyethyl)-p-toluidine and 1 g Na methylate are heated under nitrogen to 100° C. in 1 h and kept at 100°–110° C. for 2 h, subsequently heated to 140° C. in 0.5 h and kept at 140° C. for 0.5 h. 77 g ethanol distills of continuously during the heating phase beyond a temperature of 90° C. A brown resin having a gram molecular weight of 410 g/mol is obtained.

EXAMPLE 2

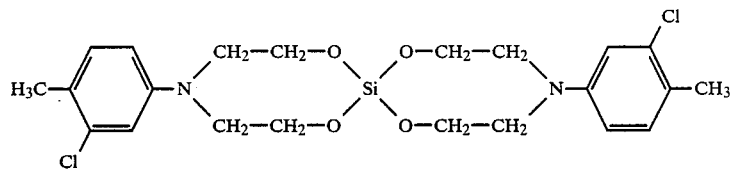

104 g silicic acid tetraethyl ester, 230.5 g N,N-bis-(β-hydroxyethyl)-m-chlorotoluidine and 1 g Na methylate are heated under nitrogen to 100° C. in 1 h and stirred at that temperature for 2 h, heated to 140° C. in 15 mins and kept at 140°–150° C. for 2.5 h. A total of 81 g ethanol distills off, leaving a dark brown resin having a gram molecular weight of 480 g/mol (theoretical 484.7 g/mol).

EXAMPLE 3

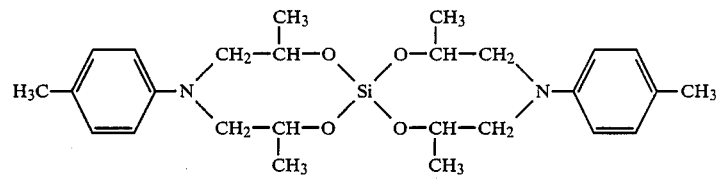

104 g silicic acid tetraethyl ester, 224 g N,N-bis-(β-hydroxyethyl)-p-toluidine and 1 g Na methylate are heated under nitrogen to 100° C. in 1 h and kept at 100° C. for 2 h. The reaction mixture is then heated to 140° C. in 0.5 h and stirred at that temperature for 2 h. 80 g ethanol distill off. A black, brittle resin having a gram molecular weight of 460 (theoretical 471.7) is obtained.

Determination of Reactivity

The gel time, hardening time and maximum temperature were determined in accordance with DIN 16 945.

The compound of Example 1 (1 for short) was used as the accelerator according to the invention. The standard accelerator A (polycondensate of adipic acid and N,N-bis-(hydroxypropyl)-p-toluidine in the form of a 70% solution in styrene) was used for comparison. Reactivity was determined by hardening the mixture of accelerator and resin with 2% of a commercial benzoyl peroxide paste (50% benzoyl peroxide content) at an initial temperature of either 0° or 25° C.

Hardening in K 36
(UP resin of Bayer AG having the following specification:
solids content: 62%
viscosity: 450–500 mPa.s
acid value: 12 mg KOH/g)

| Accelerator | % N | % in resin | Gel time mins | Hardening time mins | $T_{max}$ °C. |
|---|---|---|---|---|---|
| A | 0.06 | 2 | 11.2 | 15.6 | 110 |
| 1 | 0.13 | 2 | 2.0 | 4.6 | 102 |
| 2 | 0.12 | 2 | 45.2 | 48.6 | 78 |

Hardening in K 36
(UP resin of Bayer AG having the following specification:
solids content: 62%
viscosity: 450-500 mPa.s
acid value: 12 mg KOH/g)

| Accelerator | % N | % in resin | Gel time mins | Hardening time mins | $T_{max}$ °C. |
|---|---|---|---|---|---|
| 3 | 0.12 | 2 | 6.8 | 9.0 | 95 |

Hardening in Leguval ® K 27
(UP resin of Bayer AG having the following specification:
solids content: 70%
viscosity: 2700-3100 mPa.s
acid value: 35 mg KOH/g)

| Accelerator | % N | % in resin | Gel time 0-35° C. mins | Hardening time 0° C.-$T_{max}$ mins | Gel time 25-35° C. mins | Hardening time 25° C.-$T_{max}$ mins | $T_{max}$ °C. |
|---|---|---|---|---|---|---|---|
| A | 0.05 | 1.68 | 72.3 | 75.6 | | | 104 |
| 1 | 0.05 | 0.81 | 40.7 | 45.3 | | | 77 |
| A | 0.05 | 1.68 | | | 8.2 | 10.3 | 138 |
| 1 | 0.05 | 0.81 | | | 4.1 | 6.1 | 142 |
| A* | 0.05 | 1.68 | | | 8.7 | 12.7 | 67 |
| 1* | 0.05 | 0.81 | | | 3.7 | 7.1 | 63 |

*in the presence of sand having a grain size of 0.2 to 1 mm in mixing ratio of 3 parts sand to 1 part resin

Hardening in Roskydal ® K 14 M
(UP resin of Bayer AG having the following specification:
solids content: 65%
viscosity: 950-1150
acid value: 30 mg KOH/g

| Accelerator | % N | % in resin | Gel time 25-35° C. | Hardening time 25-$T_{max}$ | $T_{max}$ °C. |
|---|---|---|---|---|---|
| A | 0.10 | 3 | 6.8 | 9.4 | 128 |
| 1 | 0.13 | 2 | 6.4 | 9.0 | 127 |

We claim:

1. 1,7,9,15-Tetraoxa-4,12-diaza-8-silaspiro-[7.7]-pentadecanes corresponding to the following formula

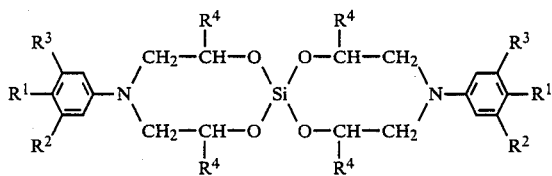

in which
R$^1$, R$^2$ and R$^3$ may be the same or different and represent hydrogen, C$_1$-C$_{18}$ alkyl, C$_5$-C$_8$ cycloalkyl, C$_5$-C$_{14}$ aryl, fluorine, chlorine, bromine or iodine and
R$^4$ represents hydrogen, C$_1$-C$_{12}$ alkyl, C$_6$-C$_{12}$ aryl, hydroxy-C$_1$-C$_6$-alkyl, chloro-C$_1$-C$_6$ alkyl, C$_1$-C$_6$-alkoxy-C$_1$-C$_6$-alkyl, C$_6$-C$_{12}$-aryloxy-C$_1$-C$_6$-alkyl or C$_2$-C$_6$-acyloxy-C$_1$-C$_6$-alkyl.

2. A process for the preparation of the new 1,7,9,15-tetraoxa-4,12-diaza-8-silaspiro-[7.7]-pentadecanes corresponding to the formula

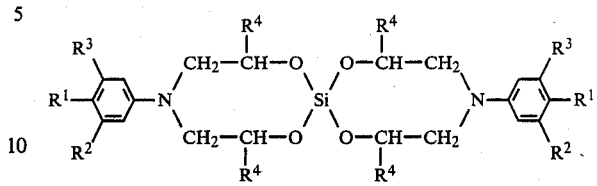

in which
R$^1$, R$^2$ and R$^3$ may be the same or different and represent hydrogen, C$_1$-C$_{18}$ alkyl, C$_5$-C$_8$ cycloalkyl, C$_5$-C$_{14}$ aryl, fluorine, chlorine, bromine or iodine and
R$^4$ represents hydrogen, C$_1$-C$_{12}$ alkyl, C$_6$-C$_{12}$ aryl, hydroxy-C$_1$-C$_6$-alkyl, chloro-C$_1$-C$_6$ alkyl, C$_1$-C$_6$-alkoxy-C$_1$-C$_6$-alkyl, C$_6$-C$_{12}$-aryloxy-C$_1$-C$_6$-alkyl or C$_2$-C$_6$-acyloxy-C$_1$-C$_6$-alkyl,
characterized in that alkoxysilanes corresponding to the formula $$Si(OR^5)_4$$

in which
R$^5$ represents C$_1$-C$_4$ alkyl,
are reacted with alkanolamines corresponding to the following formula

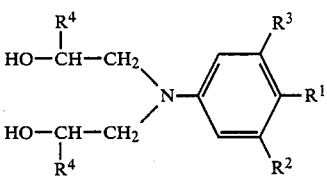

in which
R$^1$, R$^2$, R$^3$ and R$^4$ are as defined above, at temperatures of 80° to 160° C. in the presence of alkali and/or alkaline earth alcoholates.

* * * * *